United States Patent
Widdison et al.

(10) Patent No.: US 9,012,629 B2
(45) Date of Patent: Apr. 21, 2015

(54) METHODS FOR THE ACYLATION OF MAYTANSINOL

(71) Applicants: Wayne C. Widdison, Belmont, MA (US); Robert Yongxin Zhao, Lexington, MA (US)

(72) Inventors: Wayne C. Widdison, Belmont, MA (US); Robert Yongxin Zhao, Lexington, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 14/037,657

(22) Filed: Sep. 26, 2013

(65) Prior Publication Data

US 2014/0142297 A1 May 22, 2014

Related U.S. Application Data

(60) Provisional application No. 61/705,731, filed on Sep. 26, 2012.

(51) Int. Cl.
*C07D 491/12* (2006.01)
*C07D 498/16* (2006.01)
*C07D 498/18* (2006.01)

(52) U.S. Cl.
CPC ............ *C07D 498/16* (2013.01); *C07D 498/18* (2013.01)

(58) Field of Classification Search
USPC ........................................................ 540/456
See application file for complete search history.

(56) References Cited

FOREIGN PATENT DOCUMENTS

| WO | WO-2006/078809 A2 | 7/2006 |
| WO | WO-2007/021674 A2 | 2/2007 |
| WO | WO-2012/074757 A1 | 6/2012 |

*Primary Examiner* — Bruck Kifle
(74) *Attorney, Agent, or Firm* — McCarter & English, LLP; Steven G. Davis; Yu Lu

(57) ABSTRACT

Disclosed is a method of preparing an amino acid ester of maytansinol by reacting maytansinol with an N-carboxyanhydride of an amino acid (NCA) in the presence of a drying agent. Also disclosed is an improved method of preparing an amino acid ester of maytansinol in which a nucleophile is added to the reaction mixture after completion of the reaction between maytansinol and an N-carboxyanhydride of an amino acid.

39 Claims, 4 Drawing Sheets

METHODS FOR THE ACYLATION OF MAYTANSINOL

REFERENCE TO RELATED APPLICATION

This application claims the benefit of the filing date, under 35 U.S.C. §119(e), of U.S. Provisional Application No. 61/705,731, filed on Sep. 26, 2012, the entire contents of which are incorporated herein by reference.

FIELD OF INVENTION

The present invention is an improved process for preparing intermediates in the synthesis of maytansinoids and antibody conjugates thereof.

BACKGROUND OF THE INVENTION

Maytansinoids are highly cytotoxic compounds, including maytansinol and C-3 esters of maytansinol (U.S. Pat. No. 4,151,042), as shown below:

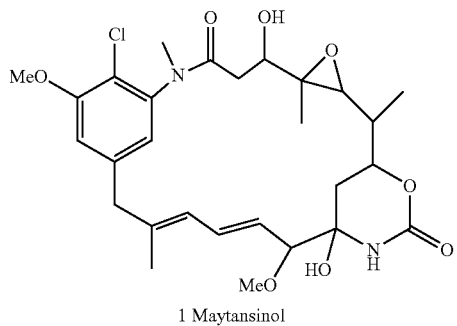
1 Maytansinol

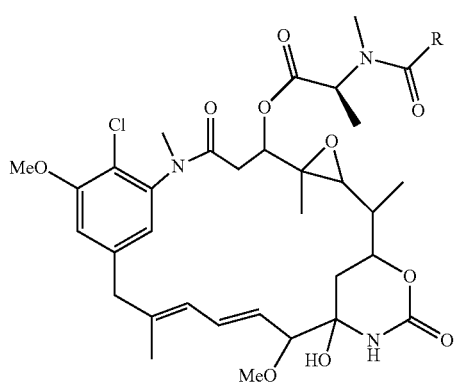
N-methyl-L-alanine side chain
2 Maytansine R = $CH_3$
3 DM1 R = $CH_2CH_2SH$
4 DM4 R = $CH_2CH_2C(CH_3)_2SH$ The naturally occurring and synthetic C-3 esters of maytansinol can be classified into two groups: (a) Maytansine (2) and its analogs (e.g., DM1 and DM4), which are C-3 esters with N-methyl-L-alanine or derivatives of N-methyl-L-alanine (U.S. Pat. Nos. 4,137,230; 4,260,608; 5,208,020; and Chem. Pharm. Bull. 12:3441 (1984)); (b) Ansamitocins, which are C-3 esters with simple carboxylic acids (U.S. Pat. Nos. 4,248,870; 4,265,814; 4,308,268; 4,308,269; 4,309,428; 4,317,821; 4,322,348; and 4,331,598).

Maytansine (2), its analogs and each of the ansamitocin species are C3 esters of maytansinol that can be prepared by esterification of maytansinol (1). U.S. Pat. Nos. 7,301,019 and 7,598,375 describe methods of acylating maytansinol (1), with an N-carboxyanhydride of an amino acid (NCA, 5), in the presence of a base to form an amino acid ester of maytansinol (May-AA, 6) as shown below:

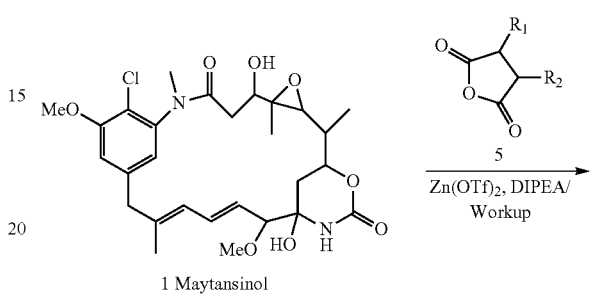
1 Maytansinol

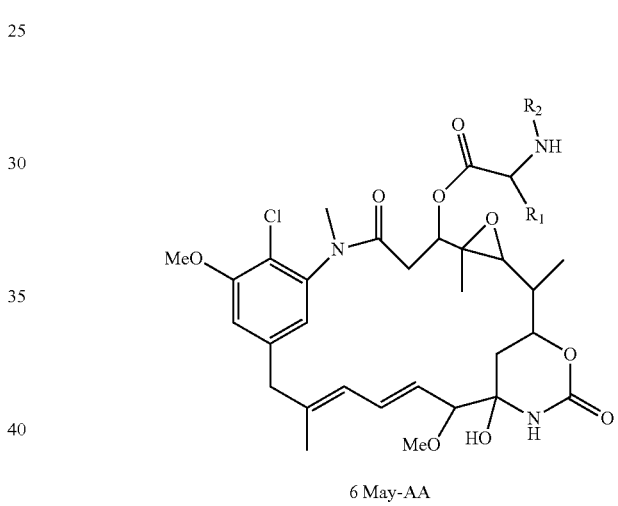
6 May-AA

Amino acid esters of maytansinol are valuable intermediates that can be coupled to carboxylic acids to provide maytansinoids. For example, reaction of maytansinol with (4S)-3,4-dimethyl-2,5-oxazolidinedione (5a) forms N2'-deacetyl-maytansine (6a), which in turn can be coupled to 3-(methyldithio)propionic acid (7), using N-(3-dimethylaminopropyl)-N'-ethylcarbodiimide hydrochloride (EDAC) to form DM1-SMe (8) as shown below:

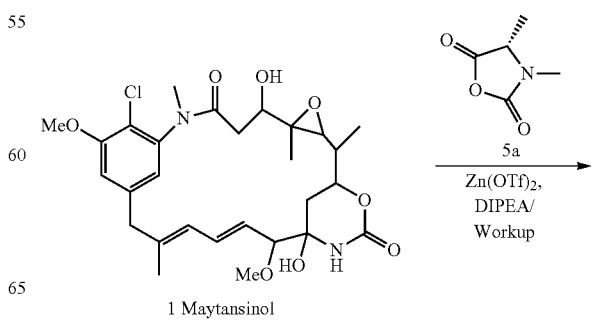
1 Maytansinol

A significant disadvantage of the acylation reaction that forms amino acid esters of maytansinol is that it also forms a by-product comprising an extra N-methyl-alanyl moiety in the C3 side chain, referred to as "extra-NMA" (9). When N2'-deacetyl-maytansine is acylated, extra NMA (9) is also acylated to form extra NMA-DM1-SMe (9a). The structures of extra-NMA (9) and extra-NMA-DM1-SMe (9a) are shown below:

DM1 (3) can be prepared from DM1-SMe (8) by reduction, which also converts any extra-NMA-DM1-SMe (9a) to extra-NMA-DM1 (10) as shown below:

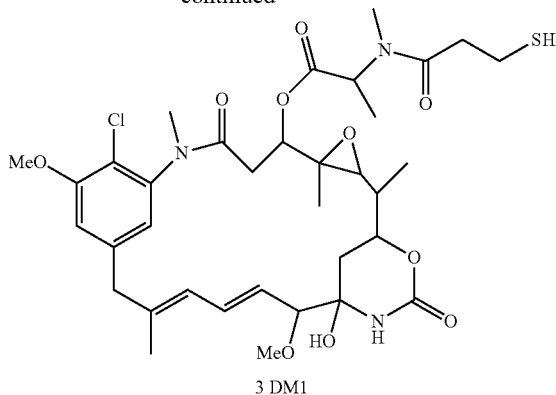

3 DM1

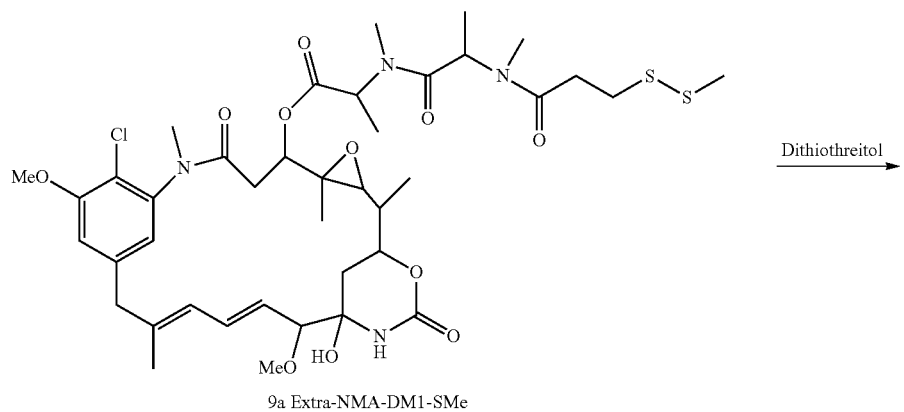

9a Extra-NMA-DM1-SMe

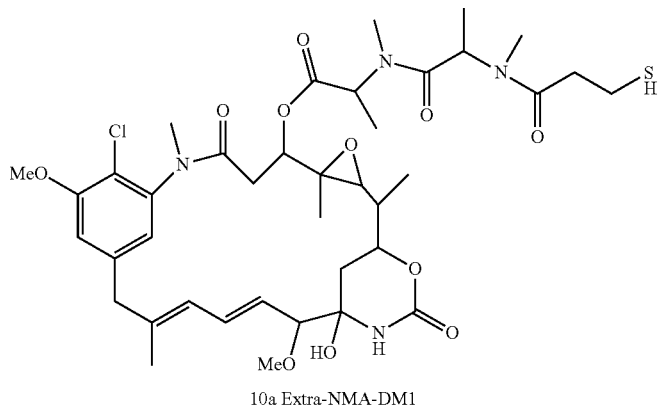

10a Extra-NMA-DM1

Extra-NMA-DM1 (10) is difficult to remove from DM1 (3) because both compounds have similar polarities and give overlapping peaks in the HPLC trace of purified DM1 (3). DM1 (3) and DM4 (4) are used to prepare antibody conjugates, several of which are currently in clinical trials.

Thus, there is a need to improve the yield and robustness of the processes to prepare such maytansinoids and to minimize by-products formed during reactions used in their preparation.

SUMMARY OF THE INVENTION

It has now been found that addition of a drying agent to the reaction between maytansinol and an N-carboxyanhydride of an amino acid substantially increases the yield of an amino acid ester of maytansinol, as shown in Examples 1-4. It has also been found that addition of a pre-quenching step with a nucleophile following the reaction of maytansinol and an N-carboxyanhydride of an amino acid substantially reduces formation of undesirable by-products, such as extra-NMA, as shown in Examples 6-8. Based on these discoveries, improved methods of preparing an amino acid ester of maytansinol are disclosed herein.

A first embodiment of the invention is a method of preparing an amino acid ester of maytansinol represented by Formula (I):

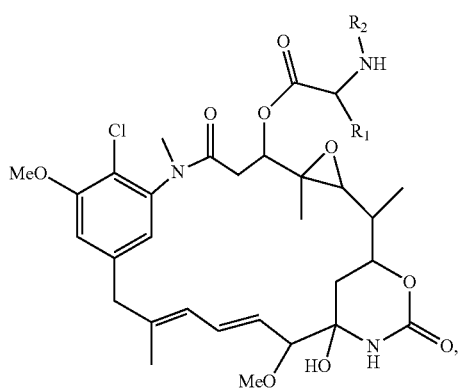
(I)

wherein $R_1$ is hydrogen, an optionally substituted C1-C10 alkyl group or an amino acid side chain, provided that, if the amino acid side chain has a functional group, the functional group is optionally protected; and $R_2$ is hydrogen or an optionally substituted C1-C10 alkyl group.

The method comprises reacting maytansinol with an N-carboxyanhydride in a reaction mixture additionally comprising a base and a drying agent. The N-carboxyanhydride is represented by the following formula:

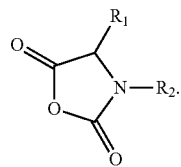
(II)

All the variables in Formula (II) are as defined in Formula (I).

A second embodiment of the invention is a method of preparing an amino acid ester of maytaninol represented by Formula (I), comprising: a) reacting maytansinol with an N-carboxyanhydride represented by Formula (II) in a reaction mixture additionally comprising a base; and b) reacting unreacted N-carboxyanhydride from step a) with a nucleophilic reagent. All the variables in Formulas (I) and (II) are as defined in the first embodiment of the invention.

DETAILED DESCRIPTION OF THE INVENTION

Figure 1:
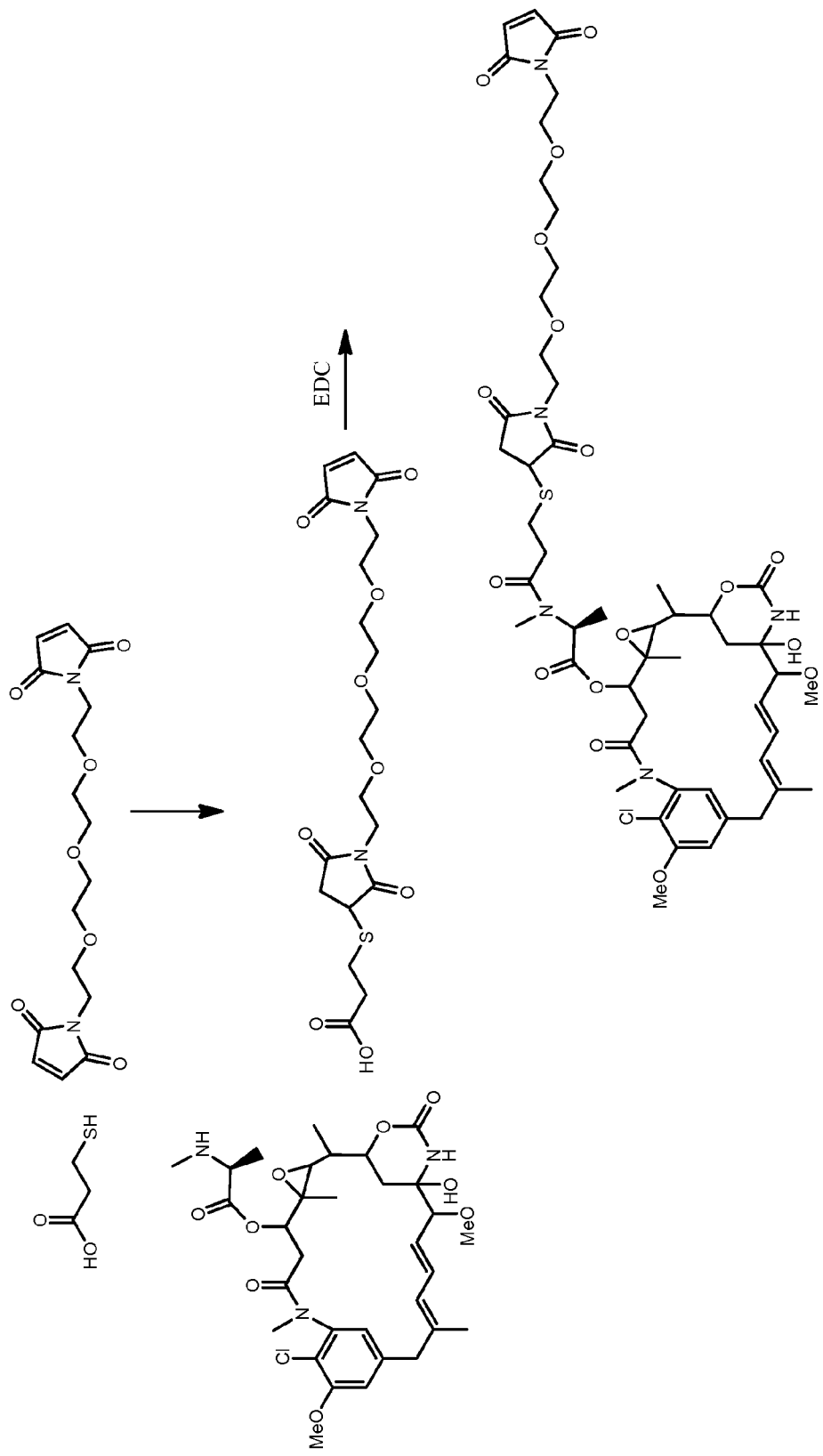
FIGS. 1-2 are schematics showing the acylation of N2'-deacetyl-maytansine with a carboxylic acid and a condensing agent.
Figure 2:
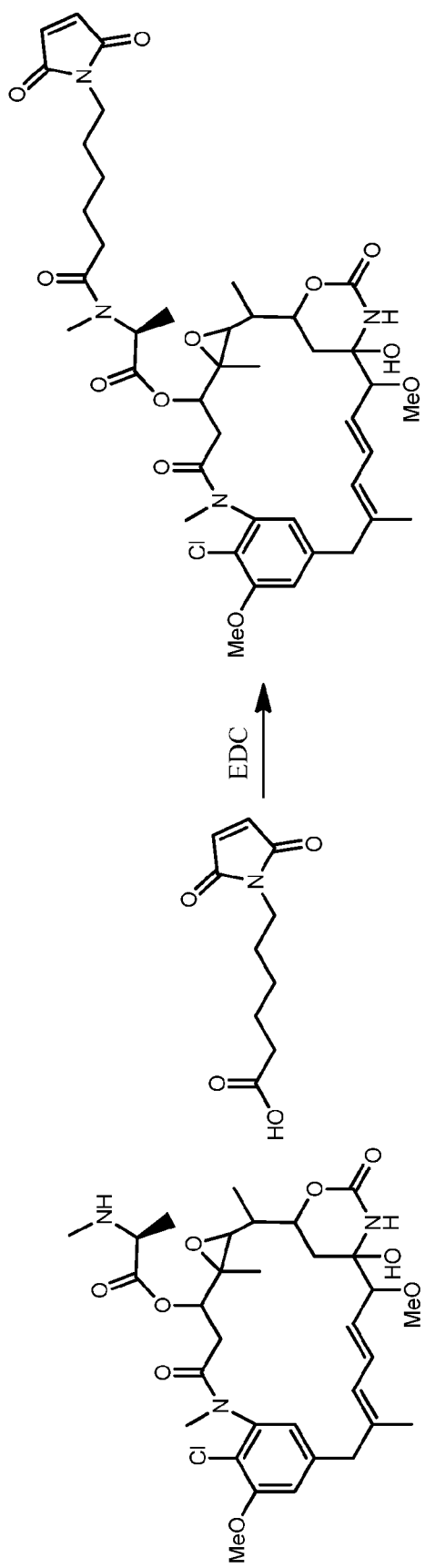
Figure 3:
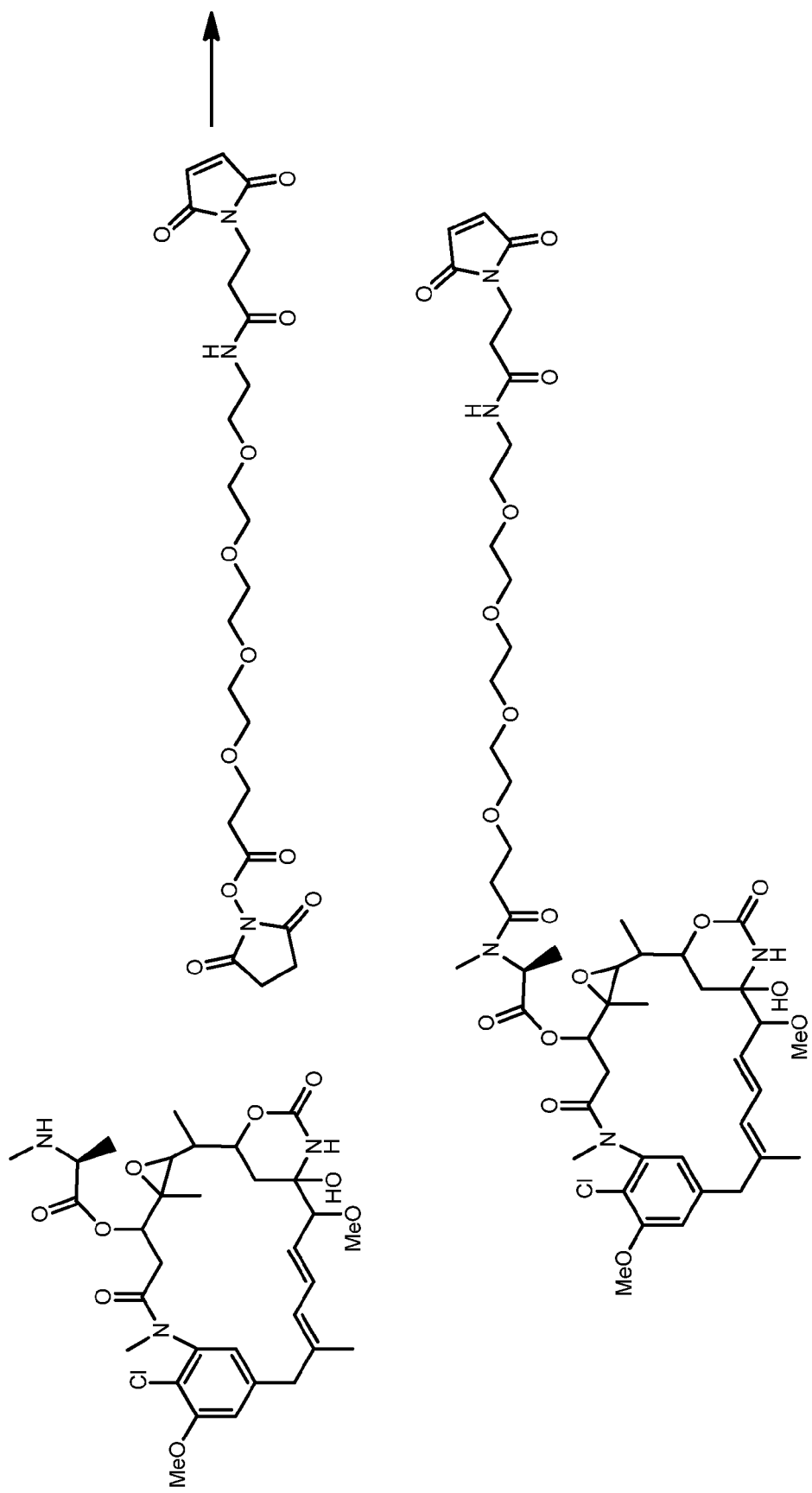
FIGS. 3-4 are schematics showing the acylation of N2'-deacetyl-maytansine with an activated carboxylic acid.
Figure 4:
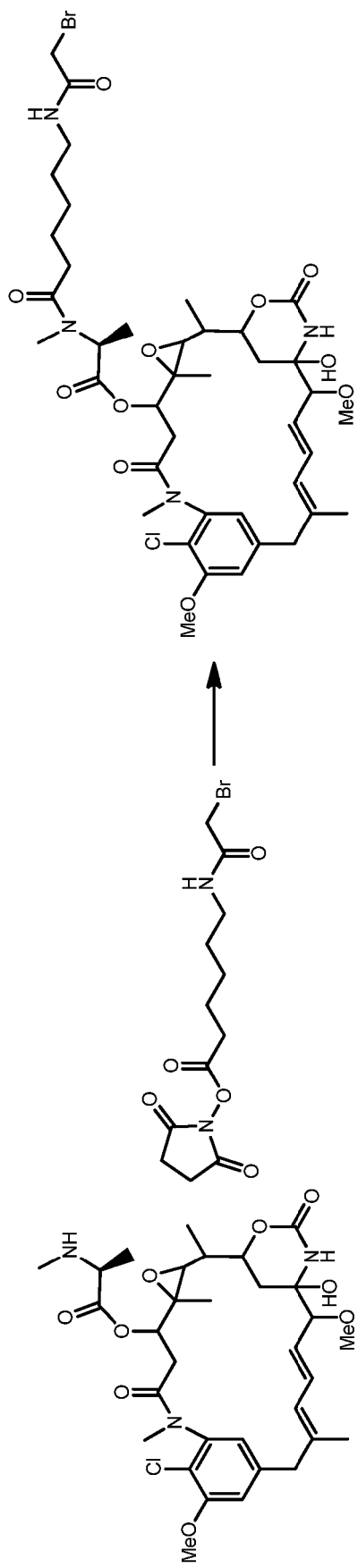

The present invention is directed to methods for preparing an amino acid ester represented by Formula (I) from maytansinol and the N-carboxyanhydride represented by Formula (II). The amino acid ester can be further esterified to prepare maytansinoids such as DM1 and DM4 and then further elaborated into antibody conjugates of maytansinoid. Preferably, the amino acid ester is represented by Formula (Ia) and the N-carboxyanhydride is represented by Formula (IIa):

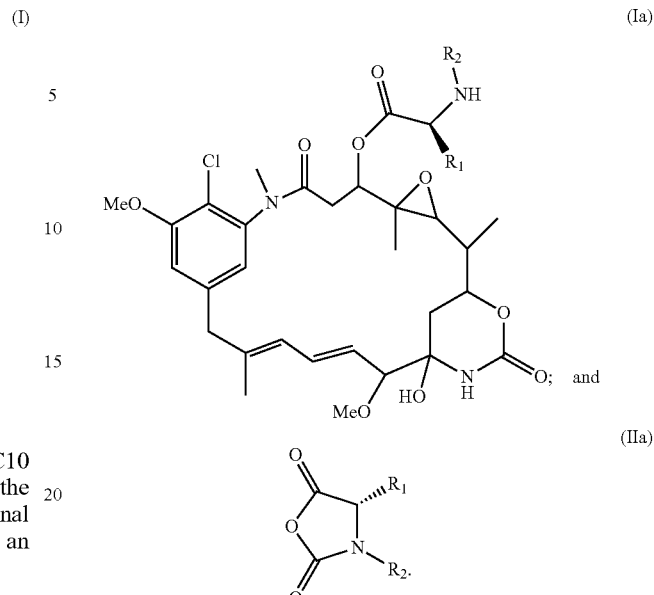

The variables in Formulas (Ia) and (IIa) are as described for Formulas (I) and (II).

Preferably for Formulas (I), (II), (Ia) and (IIa), $R_1$ is the side chain of a naturally occurring amino acid, provided that, if the side chain has a reactive functional group, the functional group is optionally protected; and $R_2$ is methyl. Alternatively, $R_1$ is alkyl and $R_2$ is methyl. More preferably, both $R_1$ and $R_2$ are methyl.

In the first embodiment of the invention, the method comprises reacting maytansinol with an N-carboxyanhydride represented by Formula (II) or (IIa) in a reaction mixture additionally comprising a base and a drying agent.

In a preferred embodiment, the reaction mixture further comprises a Lewis acid. Preferred Lewis acids comprise a metal cation.

In another preferred embodiment, maytansinol and the N-carboxyanhydride are first reacted and the reaction mixture is then contacted with an aqueous solution containing bicarbonate or carbonate or by contacting the reaction mixture with a metal scavenger. Metal scavengers known in the art can be used (see, for example, chapter 9 in "The Power of Functional Resin in Organic Synthesis" by Aubrey Mendoca, Wiley-VCH Verlag GmbH & Co. KGaA, 2008). Examples of metal scavengers include, but are not limited to, polymer and silica-based metal scavenger (e.g., QuadraPure™ and QuadraSiff™ by Sigma-Aldrich, SiliaMetS® by SiliCycle, Smopex® by Johnson Matthey and Biotage metal scavengers), carbon-based scavengers (e.g., QuadraPure™ by Sigma-Aldrich).

In another preferred embodiment, maytansinol and the N-carboxyanhydride are first reacted and the metal cation from the Lewis acid is then removed from the reaction mixture. For example, the metal cation from the Lewis acid is removed from the reaction mixture by contacting the reaction mixture with an aqueous solution containing bicarbonate or carbonate or by contacting the reaction mixture with a metal scavenger.

In the second embodiment, the method comprises: a) reacting maytansinol with an N-carboxyanhydride represented by formula (II) or (IIa) in a reaction mixture additionally comprising a base; b) reacting unreacted N-carboxyanhydride from step a) with a nucleophilic reagent.

In one preferred embodiment, the reaction mixture of step a) further comprises a Lewis acid. Preferred Lewis acids comprise a metal cation.

In another preferred embodiment, the reaction mixture after step b) is contacted with an aqueous solution containing bicarbonate or carbonate or with a metal scavenger.

In another preferred embodiment, the metal cation from the Lewis acid is removed from the reaction mixture after performing step b), i.e., after reaction of the nucleophile with the unreacted N-carboxyanhydride. For example, the metal cation from the Lewis acid is removed from the reaction mixture by contacting the reaction mixture with an aqueous solution containing bicarbonate or carbonate or by contacting the reaction mixture with a metal scavenger.

In still another preferred embodiment, the reaction mixture of step a) further comprises a drying agent.

The term "base" refers to a substance that can accept hydrogen ions (protons) or donate a pair of valence electrons. Exemplary bases are non nucleophilic and non reactive to the N-carboxyanhydride represented by Formula (II). Examples of the suitable bases include a trialkylamine (e.g., diisopropylethylamine, triethylamine, and 1,8-Diazabicycloundec-7-ene), a metal alkoxide (e.g., sodium tert-butoxide and potassium tert-butoxide), an alkyl metal (e.g., tert-butyllithium, methyl lithium, n-butyl lithium, tert-butyl lithium, lithium diisopropylamide, pentyl sodium, and 2-phenyl isopropylpotassium), an aryl metal (e.g., phenyl lithium), a metal hydride (e.g., sodium hydride), a metal amide (e.g., sodium amide, potassium amide, lithium diisopropylamide and lithium tetramethylpiperidide), and a silicon-based amide (e.g., sodium bis(trimethylsilyl)amide and potassium bis(trimethylsilyl)amide). Preferably, the base is a trialkylamine. More preferably, the base is diisopropylethylamine.

The term "drying agent" refers to an agent that can remove water from a solution. Examples of a suitable drying agent include, but are not limited to, molecular sieves, sodium sulfate, calcium sulfate, calcium chloride, and magnesium sulfate. The physical forms of the drying agents include, but are not limited to, granular beads or powders. Preferably, the drying agent is molecular sieve. Alternatively, the drying agent is sodium sulfate.

The term "Lewis acid" refers to an acid substance which can employ an electron lone pair from another molecule in completing the stable group of one of its own atoms. Exemplary Lewis acids for use in the disclosed methods include zinc triflate, zinc chloride, magnesium bromide, magnesium triflate, copper triflate, copper (II) bromide, copper (II) chloride, and magnesium chloride. Preferably, the Lewis acid is zinc triflate.

The term "nucleophilic reagent" refers to a reactant that reacts with electropositive centers in the N-carboxyanhydride represented by Formula (II) to decompose the N-carboxyanhydride. Examples of suitable nucleophilic reagent include water, an alcohol (methanol, ethanol, n-propanol, isopropanol, or tert-butanol) and a primary or secondary amine (e.g., methylamine, ethylamine, dimethylamine, diethylamine, etc.). Preferably, the nucleophilic reagent is an alcohol. Alternatively, the nucleophilic reagent is water.

Exemplary reaction conditions for preparing the amino acid esters of maytansinol represented by Formula (I) are provided below. Specific conditions are provided in Exemplification.

Although equimolar amounts of maytansinol to an N-carboxyanhydride can be used, more commonly N-carboxyanhydride is used in excess. Exemplary molar ratios of maytansinol to N-carboxyanhydride range from 1:1 to 1:10, more commonly 1:2 to 1:7 or 1:1 to 1:4. In a preferred embodiment, the molar ratio of maytansinol to N-carboxyanhydride is about 1:5.

The Lewis acid is used optionally in the disclosed methods. When present, it is typically used in excess relative to the maytansinol, for example, up to a 20 fold excess. More commonly, the molar ratio of maytansinol to Lewis acid ranges from 1:5 to 1:8, more preferably about 1:7. Lesser amounts of Lewis acid can also be used.

Sufficient amounts of drying agents are used to remove dissolved water from the reaction solvent. The quantity of drying agent is not critical, provided that the reaction solution is rendered substantially anhydrous. The drying agent can be used directly in the reaction vessel or by being contained in the vessel by a semi permeable barrier, such as a sintered glass container.

The time required for the reaction can be easily monitored by one skilled in the art using techniques including, but not limited to, high pressure liquid chromatography and thin layer chromatography. A typical reaction is completed after stirring for 24 hours but may be performed at a slower or a faster rate depending on various factors, such as reaction temperature and concentrations of the reactants.

The reaction can be performed between −20° C. through 80° C., preferably between −10° C. and 60° C., more preferably between −10° C. to 40° C., and most preferably between 0° C. and 35° C.

Suitable solvents are readily determined by one of ordinary skill in the art, and include, but are not limited to, polar aprotic solvents such as anhydrous dimethyl formamide, dimethyl sulfoxide (DMSO) or dimethylacetamide (DMA), hexanes, ethers (such as tetrahydrofuran, diethyl ether, dimethoxyethane, dioxane), dichloromethane, or a mixture thereof.

If a Lewis acid is present in the reaction mixture, the reaction mixture after the reaction of maytansinol and the N-carboxyanhydride is preferably contacted with an aqueous solution containing bicarbonate or carbonate or with a metal scavenger. Preferably, the reaction mixture is reacted with the nucleophilic reagent to decompose excess N-carboxyanhydride prior to the reaction mixture being contacted with an aqueous solution containing bicarbonate or carbonate or with a metal scavenger.

If a Lewis acid comprising a metal cation is present in the reaction mixture, the metal cation is preferably removed from the reaction mixture as part of the reaction work-up. Removal of the metal cation can be accomplished by contacting the reaction mixture with an aqueous solution containing bicarbonate or carbonate or with a metal scavenger. Preferably, the N-carboxyanhydride is reacted with the nucleophilic reagent prior to removal of the metal cation.

The amount of a nucleophile in step b) can be readily determined by a skilled person in the art. Preferably, a sufficient quantity of nuclophile is used to decompose the unreacted N-carboxyanhydride. This is typically an equimolar quantity of nucleophile, however, excess quantities of nucleophile can also be used. A typical reaction is completed after stirring 1 hour but may be performed at a slower or a faster rate depending on various factors, such as temperature.

Also, within the scope of the invention is a method of acylating the amino acid ester of maytansinol. The method comprises reacting an amino acid ester of maytansinol represented by Formula (I) or Formula (Ia) prepared as described above with a carboxylic acid, having the formula "$R_3COOH$", in the presence of a condensing agent or with an activated carboxylic acid having the formula "R₃COX", to form a compound represented by one of the following formulas, respectively:

(III)
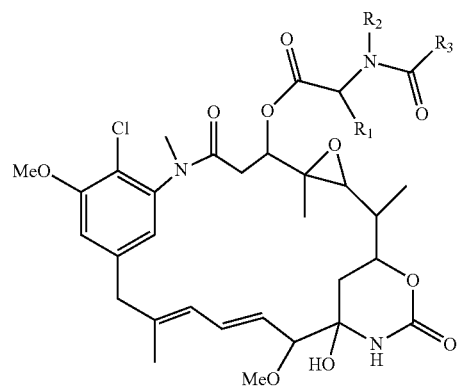

and (IIIa)
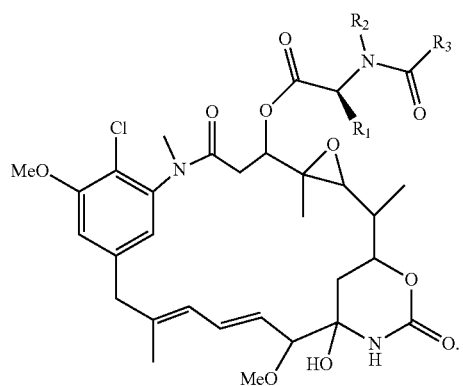

In Formula (III) or (IIIa), R₁ and R₂ are as defined in Formulas (I), (II), (Ia), and (IIa); R₃ is an alkyl group or a substituted alkyl group; and X in R₃COX is a leaving group. Preferably, X is a halide, an alkoxy group, an aryloxy group, an imidazole, —S-phenyl, in which phenyl is optionally substituted with nitro or chloride, or —OCOR, in which R is a linear C1-C10 alkyl group, a branched C1-C10 alkyl group, a cyclic C3-C10 alkyl group, or a C1-C10 alkenyl group. In one embodiment, in the formula "R₃COX" described above, —COX is a reactive ester; for example an optionally substituted N-succinimide ester. Examples of a reactive ester include, but are not limited to, N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl and 3-carboxy-4-nitrophenyl esters.

Preferably, R₃ is —Y—S—SR₄, Y is C1-C10 alkylene, and R₄ is C1-C10 alkyl, aryl, or heteroaryl. In another alternative, Y is —CH₂CH₂— or —CH₂CH₂C(CH₃)₂— and R₄ is methyl.

In another embodiment, R₃ is -L-E; L is or

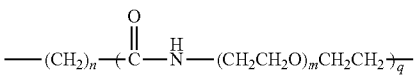

—(CH₂CH₂O)ₘCH₂CH₂NHC(=O)CH₂CH₂— or

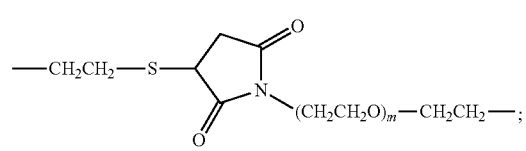

E is

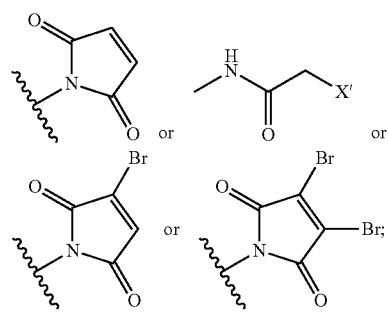

X' is a halide; n is 1, 2, 3, 4, 5 or 6; m is 0 or an integer from 1 to 20; and q is 0 or 1. Alternatively, L is —(CH₂)ₙ—; and n is as defined above or n is 5. In another alternative, L is

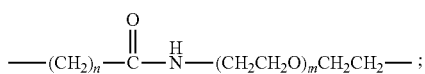

and n and m are as defined above; or, alternatively, n is 4 and m is 3.

In yet another alternative, R₃ is selected from the following formulas:

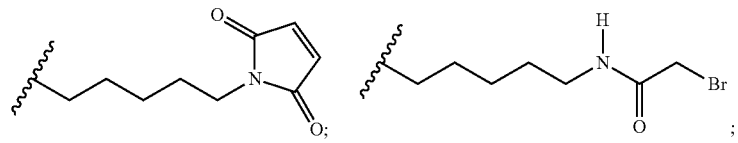

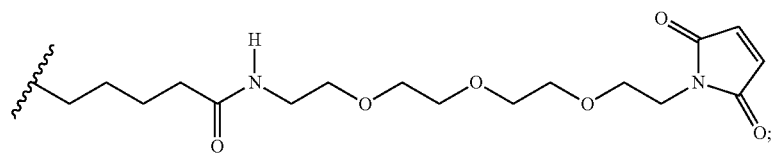

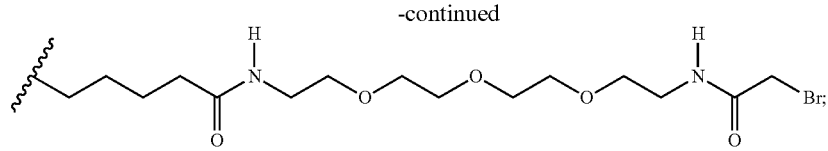

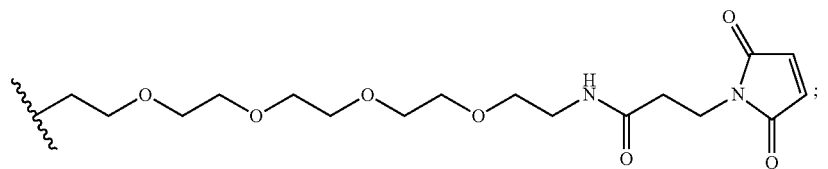

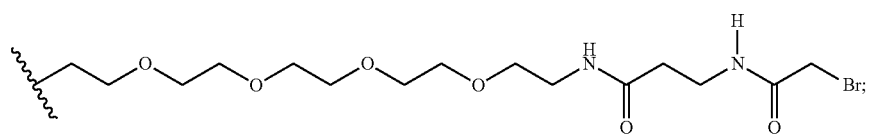

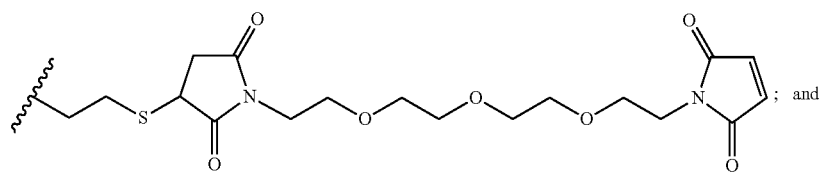

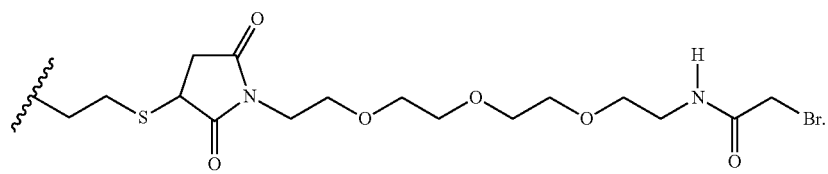

The term "condensing agent" is a reagent that reacts with the hydroxyl group of a carboxylic acid and converts it into a leaving group, which can be displaced by an amine or a hydroxyl group. Examples of suitable condensing agents include a carbodiimide (N-(3-dimethylaminopropyl)-N'-ethylcarbodiimide hydrochloride), a uronium, an active ester, a phosphonium, 2-alkyl-1-alkylcarbonyl-1,2-dihydroquinoline (2-isobutoxy-1-isobutoxycarbonyl-1,2-dihydroquinoline), 2-alkoxy-1~alkoxycarbonyl-1,2-dihydroquinoline (2-ethoxy-1~ethoxycarbonyl-1,2-dihydroquinoline), or alkylchloroformate (isobutylchloroformate). Preferably, the condensing agent is a carbodiimide. More preferably, N-(3-dimethylaminopropyl)-N'-ethylcarbodiimide hydrochloride.

The term "leaving group" refers to a group of charged or uncharged moiety that can readily be displaced by a nucleophile, such as an amine. Such leaving groups are well known in the art and include, but not limited to, halides, esters, alkoxy, hydroxyl, alkoxy, tosylates, triflates, mesylates, nitriles, azide, an imidazole, carbamate, disulfides, thioesters, thioethers (i.e., —S-phenyl optionally substituted) and diazonium compounds. Preferably, the leaving group is a halide, an alkoxy group, an aryloxy group, an imidazole, —S-phenyl optionally substituted with —NO$_2$ or Chloro, or —OCOR, in which R is a linear C1-C10 alkyl group, a branched C1-C10 alkyl group, a cyclic C3-C10 alkyl group, or a C1-C10 alkenyl group. In another preferred embodiment, the leaving group is the moiety in a reactive ester (e.g., —COX) that can be displaced. A reactive ester includes, but is not limited to N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl and 3-carboxy-4-nitrophenyl ester.

The invention also includes a method of using a C3 ester of maytansinol to prepare a derivative thereof. The method comprises reacting a C3 ester of maytansinol represented by Formula (III) or (IIIa) prepared above with a reducing agent to form a compound represented by one of the following formulas:

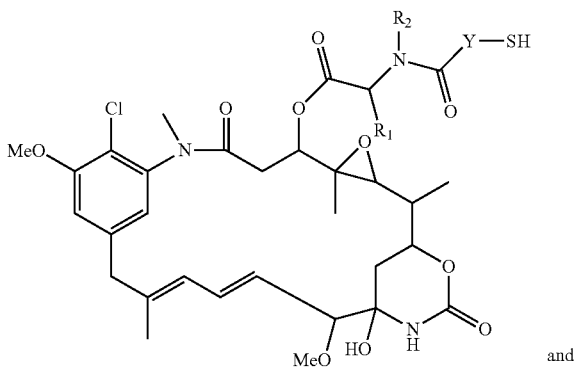

and

-continued (IVa)

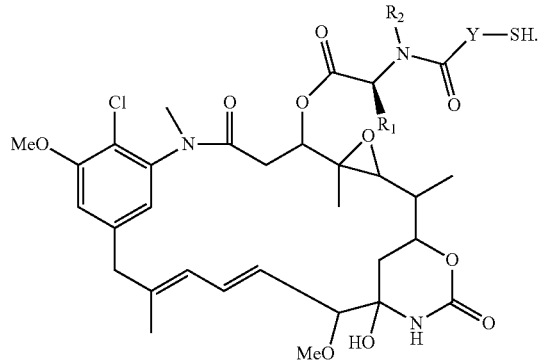

In Formula (IV) and (IVa), $R_1$ and $R_2$ are as defined in Formulas (I), (II), (Ia), and (IIa); and Y is as defined in Formula (III) or (Ma).

The term "reducing agent" is the element or compound in a reduction-oxidation reaction that convert a disulfide bond to a hydrosulfide group. Examples of suitable reducing agents include dithiothreitol (DTT), (tris(2-carboxyethyl)phosphine) (TCEP) and $NaBH_4$.

The compound of formula (III) or (Ma), when $R_3$ is -L-E, or the compound of formula (IV) or (IVa) can react with an antibody or a modified antibody to form an antibody-maytansinoid conjugate. See for example, U.S. Pat. Nos. 7,521,541, 5,208,020, and 7,811,872. Alternatively, the compound of formula (IV) or (IVa) can react with a bifunctional crosslinker to form a linker compound carrying a reactive group that can react with an antibody to form an antibody-maytansinoid conjugate. See, for example, U.S. Pat. No. 6,441,163, US 2011/0003969A1 and US 2008/0145374.

"Alkyl" as used herein refers to a linear, branched or cyclic alkyl.

"Linear or branched Alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —$CH_2CH(CH_3)_2$, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, —$CH_2CH_2CH(CH_3)_2$, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Alkylene" as used herein refers to a linear, branched or cyclic alkylene.

"Linear or branched Alkylene" as used herein refers to a saturated linear or branched-chain divalent hydrocarbon radical of one to twenty carbon atoms. Examples of alkyl include, but are not limited to, methylene, ethylene, 1-propylene, 2-propylene, 1-butylene, 2-methyl-1-propylene, —$CH_2CH(CH_3)_2$—, 2-butylene, 2-methyl-2-propylene, 1-pentylene, 2-pentylene, 3-pentylene, 2-methyl-2-butylene, 3-methyl-2-butylene, 3-methyl-1-butylene, 2-methyl-1-butylene, —$CH_2CH_2CH(CH_3)_2$—, 1-hexyl, 2-hexylene, 3-hexylene, 2-methyl-2-pentylene, 3-methyl-2-pentylene, 4-methyl-2-pentylene, 3-methyl-3-pentylene, 2-methyl-3-pentylene, 2,3-dimethyl-2-butylene, 3,3-dimethyl-2-butylene, 1-heptylene, 1-octylene, and the like. Preferably, the alkylene has one to ten carbon atoms. More preferably, the alkylene has one to four carbon atoms.

"Linear or branched Alkenyl" refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like. Preferably, the alkenyl has two to ten carbon atoms. More preferably, the alkenyl has two to four carbon atoms.

"Cyclic alkyl" refers to a monovalent saturated carbocyclic ring radical. Preferably, the cyclic alkyl is three to ten membered monocyclic ring radical. More preferably, the cyclic alkyl is cyclohexyl.

"Aryl" means a monovalent aromatic hydrocarbon radical of 6-18 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes (e.g., para-nitrophenyl, ortho-nitrophenyl, and dinitrophenyl), naphthalene, anthracene, indenyl, indanyl, 1,2-dihydronapthalene, 1,2,3,4-tetrahydronapthyl, and the like. Preferably, the aryl is optionally substituted phenyl (e.g., phenyl, phenol or protected phenol).

"Heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (e.g., 2-hydroxypyridinyl), imidazolyl, imidazopyridinyl, pyrimidinyl (e.g., 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

Suitable substituents for an alkyl group are those which do not significantly interfere with the disclosed reactions. Substituents that do interfere with the disclosed reactions can be protected according to methods well known to one of ordinary skill in the art, for example, in T. W. Greene and P. G. M. Wuts "Protective Groups in Organic Synthesis" John Wiley & Sons, Inc., New York 1999. Exemplary substituents include aryl (e.g., phenyl, phenol and protected phenol), heteroaryl (e.g., indolyl and imidazolyl) halogen, guanidinium [—NH(C=NH)$NH_2$], —$OR^{100}$, $NR^{101}R^{102}$, —$NO_2$, —$NR^{101}COR^{102}$, —$SR^{100}$, a sulfoxide represented by —$SOR^{101}$, a sulfone represented by —$SO_2R^{101}$, a sulfate —$SO_3R^{100}$, a sulfonate —$OSO_3R^{100}$, a sulfonamide represented by —$SO_2NR^{101}R^{102}$, cyano, an azido, —$COR^{101}$, —$OCOR^{101}$, —$OCONR^{101}R^{102}$; $R^{101}$ and $R^{102}$ are each independently selected from H, linear, branched or cyclic alkyl, alkenyl or alkynyl having from 1 to 10 carbon atoms.

The term "halide" refers to —F, —Cl, —Br or —I.

The term "amino acid" refers to naturally occurring amino acids or non-naturally occurring amino acid represented by $NH_2$—$C(R^{aa'}R^{aa})$—$C(=O)OH$, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl. The term "amino acid" also refers to the corresponding residue when one hydrogen atom is removed from the amine and/or carboxy end of the amino acid, such as —NH—C($R^{aa'}R^{aa}$)—C(=O)O—. The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXEMPLIFICATION

Materials and Methods

The process parameters given below can be adopted and adapted by skilled persons to suit their particular needs.

All reactions were performed under an argon atmosphere with magnetic stirring. Tetrahydrofuran and dimethyl formamide were purchased as anhydrous solvents from Aldrich. Maytansinol, was produced as described (Widdison et al., *J. Med. Chem.*, 49:4392-4408 (2006)). The N-carboxyanhydride of N-methyl-alanine, (4S)-3,4-dimethyl-2,5-oxazolidinedione was prepared as described (Akssira, M. et al., *J. Marocain de Chimie Heterocyclique*, 1:44-47 (2002)). Nuclear magnetic resonance (NMR) spectra ($^1$H 400 MHz, $^{13}$C 100 MHz) were obtained on a Bruker ADVANCE™ series NMR. HPLC/MS data was obtained using a Bruker ESQUIRE™ 3000 ion trap mass spectrometer in line with an Agilent 1100 series HPLC. HPLC method 1 was used to analyze DM1. HPLC method 2 was used for all other analyses.

Analytical HPLC Method 1:
Water HPLC system with UV detector or equivalent
Column: YMC-Pack ODS-AQ 250×4.6 mm; 5 μm (Part #=AQ12S05-2546WT)
Flow: 1 mL/min (Gradient)
Mobile Phase: A=1 ml of 85% $H_3PO_4$ in 1 liter water; B=acetonitrile/Tetrahydrofuran 30:70 (v/v) (Note: 0.1% TFA was used instead of H3PO4 in the mobile phase A in LC/MS analysis
Gradient Table:

| | Time, min | Flow | % A | % B |
|---|---|---|---|---|
| 1 | 0.0 | 1.00 | 62 | 38 |
| 2 | 25 | 1.00 | 62 | 38 |
| 3 | 40 | 1.00 | 40 | 60 |
| 4 | 60 | 1.00 | 40 | 60 |

Run time: 60 minutes+Post time: 10 minutes
UV detection: 252 nm
Injection volume=5 μL of about 1 mg/ml of DM1 in acetonitrile
Column temperature=15° C. (unless otherwise stated)
Sample temperature=2-8° C.
Analytical HPLC/MS Method 2:
Column: 150×4.6 mm C8, particle size 5 micron, Zorbax P/N 993967-906
Solvents: A deionized water+0.1% TFA
Solvent B: Acetonitrile
Flow rate 1.0 mL/min Temperature: Ambient
Injection volume: 15 μL

| Gradient | |
|---|---|
| Time | % B |
| 0 | 25 |
| 25 | 50 |
| 26 | 95 |
| 30 | 95 |
| 31 | 25 |
| 37 | 25 |

Data was displayed from 0-25 min in HPLC traces.
Sample Preparation for Analytical HPLC Method 2:
Aliquots (20 μL) of a given mixture were added to acetonitrile (1.5 mL) in an autosampler vial. The vial was capped and shaken then placed in a 15° C. autosampler. An injection volume (15 μL) was analyzed for each HPLC run.

Example 1

Preparation of DM1-SMe with Added 4a Molecular Sieves as Drying Agent

Maytansinol (50.1 mg, 0.0888 mmol), (4S)-3,4-dimethyl-2,5-oxazolidinedione (30.2 mg, 0.233 mmol, 2.6 eq), zinc triflate (133 mg, 0.366 mol) and 4A Molecular sieves (0.50 g) pre-dried at 250° C. under vacuum then cooled to ambient temperature, were added to a 10 ml flask. The contents were taken up in anhydrous dimethyl formamide (0.75 mL) to which was added diisopropylethyl amine (62 μL, 0.357 mmol). The mixture was stirred at ambient temperature for 24 hrs. A sample of the crude mixture was analyzed by HPLC, $N^{2'}$-deacetyl-maytansine product accounted for 80% of the total HPLC area. The reaction mixture was diluted with 1:1 saturated $NaHCO_3$:saturated NaCl (1.2 mL) and ethyl acetate (3 mL) mixed then filtered with celite, then washed with potassium phosphate buffer (1 mL, 400 mM, pH 7.5). The organic layer was dried with anhydrous magnesium sulfate, filtered then evaporated to form a yellow solid. To the solid was added 3-methyldithiopropanoic acid (25 mg, 0.16 mmol), N-(3-dimethylaminopropyl)-N'-ethylcarbodiimide hydrochloride (30 mg, 0.16 mmol) and dichloromethane (3 mL). After stirring for 2 hrs., the mixture was diluted with ethylacetate (8 mL), washed with 1.0 M, pH 6.5 potassium phosphate buffer (2 mL) and the aqueous solution was extracted with ethyl acetate (2×8 mL). The organic layers were combined, dried over anhydrous magnesium sulfate, concentrated and purified by silica chromatography 95:5 dichloromethane:methanol to afford 51 mg (70%) of DM1-SMe.

Example 2

10× Scale Up of Example 1

The reaction in Example 1 was run on a 10 fold larger scale giving 490 mg (68%) of DM1-SMe.

Example 3

Preparation of DM1-SMe without Added Drying Agent

Maytansinol (1.0 g, 1.77 mmol) was dissolved in anhydrous dimethyl formamide (15 mL) in a 25 mL flask which was cooled in an ice/water bath. After 2 min diisopropylethyl amine (DIPEA, 0.92 g 7.07 mmol) and zinc triflate (3.8 g, 10.6 mmol) were added with magnetic stirring, then (4S)-3,4-dimethyl-2,5-oxazolidinedione (0.913 g, 7.07 mmol) was quickly added and the mixture was stirred for 24 hrs. A sample of the crude mixture was analyzed by HPLC, $N^{2'}$-deacetyl-maytansine product accounted for 65% of the total HPLC area. The reaction mixture was diluted with 1:1 saturated NaHCO$_3$: saturated NaCl (25 mL) and ethyl acetate (40 mL), mixed then filtered with celite, and washed with saturated NaCl. The organic layer was dried with anhydrous sodium sulfate, filtered then evaporated. Residue was taken up in dichloromethane (30 mL) to which 3-methyldithiopropanic acid (1.1 g, 7.0 mmol) and N-(3-dimethylaminopropyl)-N'-ethylcarbodiimide hydrochloride (1.34 g, 7.0 mmol) were quickly added and the reaction was stirred under argon at ambient temperature for 2 hours. The mixture was diluted with ethyl acetate (30 mL), washed with 1.0 M potassium phosphate buffer (30 mL), pH 6.5, and the aqueous solution was extracted with ethyl acetate (2×40 mL). The organic layers were combined, dried over anhydrous sodium sulfate, concentrated and purified by silica chromatography 95:5 dichloromethane:methanol to afford 698 mg (50%) of DM1-SMe.

Example 4

Repeat of Example 3

The reaction in Example 3 was repeated on the same scale giving 735 mg (53%) of DM1-SMe.

Example 5

Crude N2'-Deacetyl-Maytansine Stock Solution

Maytansinol (0.5 g, 0.89 mmol) was dissolved in anhydrous dimethyl formamide (7 mL) in a 25 mL flask which was cooled in an ice/water bath. After 2 min diisopropyl ethyl amine (0.5 g, 3.5 mmol) and zinc triflate (1.9 g, 5.3 mmol) were added with magnetic stirring, then (4S)-3,4-dimethyl-2,5-oxazolidinedione (4.52 g, 3.5 mmol) was quickly added and the mixture was stirred for 24 hrs. Aliquots (0.5 mL each) of this stock solution were used in the following experiments thus each aliquot was generated from approximately 0.13 mmol of maytansinol.

Example 6

$N^{2'}$-Deacetyl-Maytansine Extraction Followed by Coupling to Propionic Acid (Control)

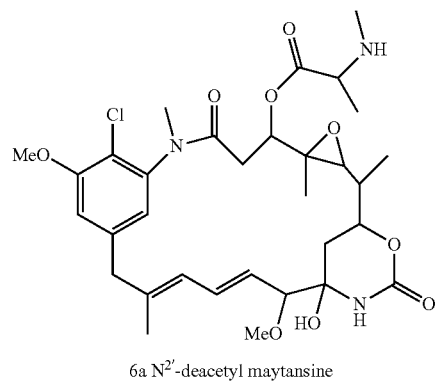

6a N$^{2'}$-deacetyl maytansine

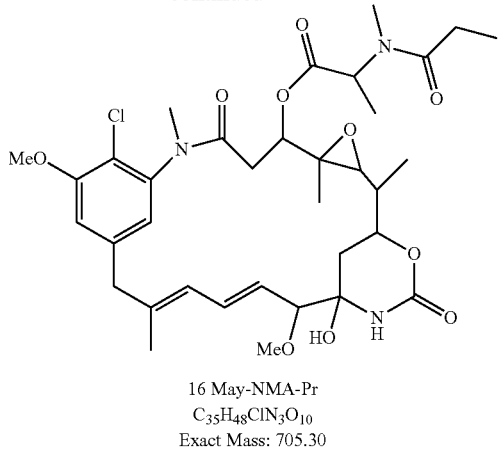

16 May-NMA-Pr
C$_{35}$H$_{48}$ClN$_3$O$_{10}$
Exact Mass: 705.30

$N^{2'}$-deacetyl-maytansine stock solution (0.50 mL) was added to a 6 mL capacity vial containing ethyl acetate (1.5 mL) and 1:1 saturated NaCl:NaHCO$_3$ (0.75 mL), quickly capped and mixed. The organic layer was retained and dried over anhydrous Na$_2$SO$_4$ (120 mg). Organic layer (1.0 mL) was taken and propionic acid (20.0 µL, 0.27 mmol). The solution was then transferred to a vial containing N-(3-dimethylaminopropyl)-N'-ethylcarbodiimide hydrochloride (40 mg, 0.209 mmol). The reaction was allowed to progress for 2.5 hrs. after which it was analyzed by HPLC.

The following by-product was also produced from May-NMA2, a by-product in the preceding reaction, as shown below:

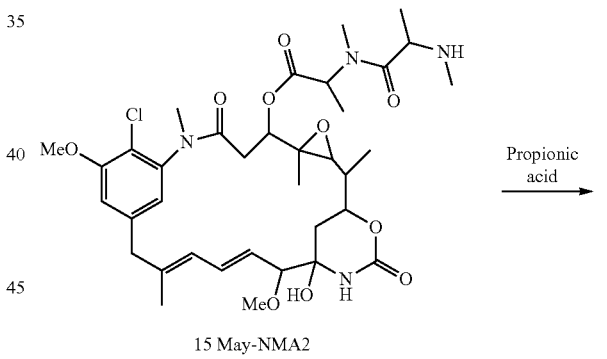

15 May-NMA2

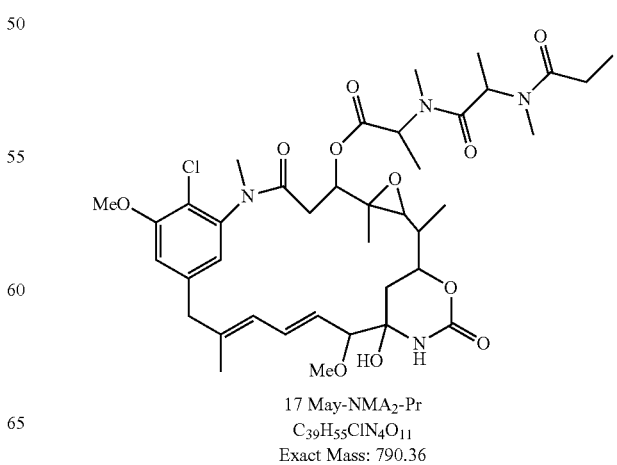

17 May-NMA$_2$-Pr
C$_{39}$H$_{55}$ClN$_4$O$_{11}$
Exact Mass: 790.36

The ratio of HPLC percent areas for 17:16 was 3.0:71.7. MS of 16 (M+H+) 706 (M+Na+) 728; MS of 17 (M+Na+) 813.

Example 7

The Experiment of Example 6 was Repeated

The ratio of HPLC percent areas for 17:16 was 3.0:70.9.

Example 8

N²'-Deacetyl-Maytansine Extraction Followed by a Methanol Pre-Quench then Coupling to Propionic Acid (Pre-Quench to Destroy Excess 5a)

N²-deacetyl-maytansine stock solution (0.50 mL) was added to a 6 mL capacity vial to which methanol (75 μL, 1.8 mmol) was added and the vial was capped and contents magnetically stirred for 1 hour. Ethyl acetate (1.5 mL) and 1:1 saturated NaCl:NaHCO₃ (0.75 mL) were then added and the vial was capped and mixed. The organic layer was retained and dried over anhydrous Na₂SO₄ (120 mg). Organic layer (1.0 mL) was taken and propionic acid (20.0 μL, 0.27 mmol) was added. The solution was then transferred to a vial containing N-(3-dimethylaminopropyl)-N'-ethylcarbodiimide hydrochloride (40 mg, 0.209 mmol). The reaction was allowed to progress for 2.5 hrs. after which it was analyzed by HPLC. The HPLC peak for 17 was barely detectable, integration was not possible. This reaction was repeated and again 17 was barely detectable, integration was not possible. Thus, the pre-quenching method produces less undesirable compounds 15 and 17.

Example 9

Synthesis of Extra-NMA-DM1-SMe (9a)

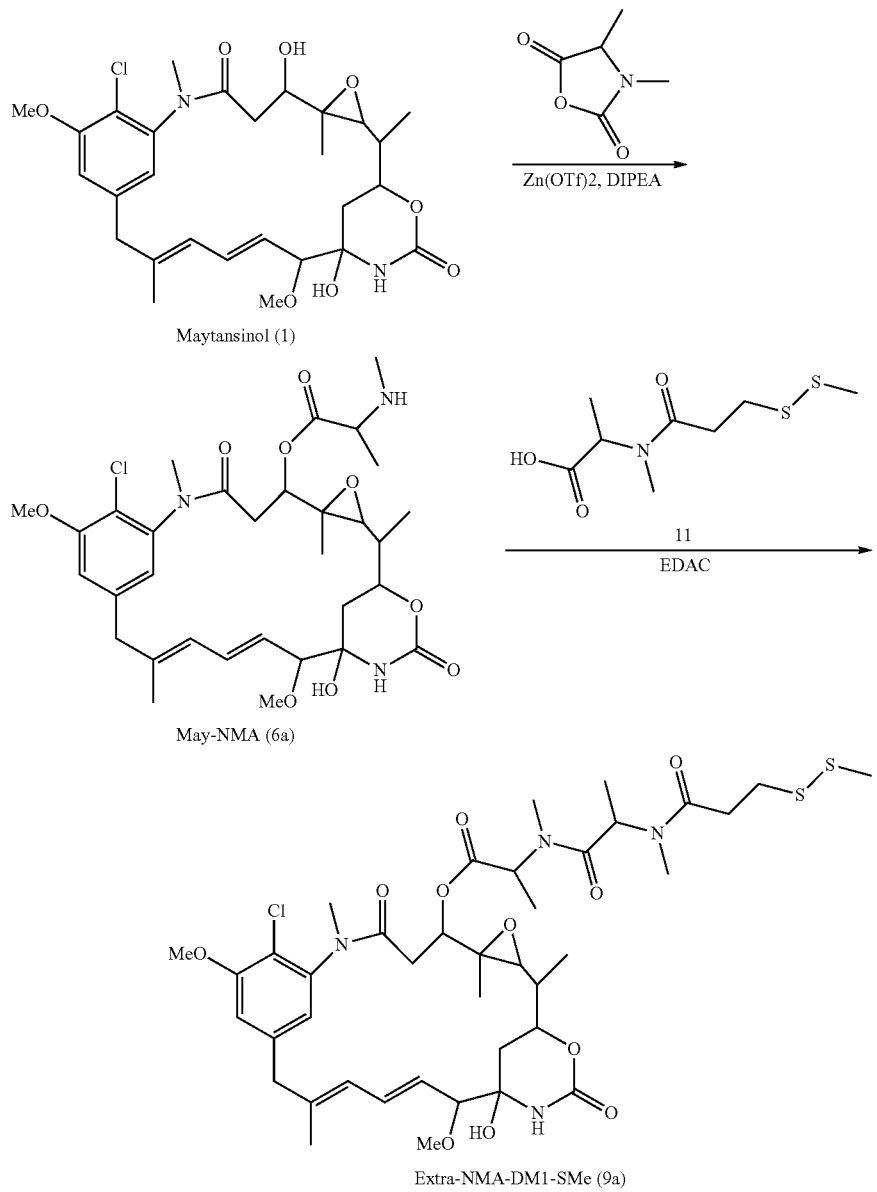

Maytansinol (1.2 mg, 2.1 mmol) was weighed into a 50 mL flask and dissolved in a mixture of dimethylformamide (12 mL) and tetrahydrofuran (6 mL). The flask was cooled in an ice/water bath. After 5 min diisopropyl ethyl amine (1.5 mL, 8.5 mmol), zinc trifluoromethanesufonate (4.5 g, 12.6 mmol), and 2,5-oxazolidinedione, 3,4-dimethyl (4S) (1.1 g, 8.5 mmol) were sequentially added. After stirring for 17 hours the reaction was extracted with 1:1 saturated aqueous NaCl: saturated aqueous NaHCO$_3$ (14 mL) and Ethyl acetate (100 mL). The organic layer was retained and dried over anhydrous Na$_2$SO$_4$. Drying agent was removed and approximately ⅔rds of the solvent was removed by rotary evaporation under vacuum. Then N-methyl-N-[(2-methyldithio)-1-oxopropyl]-L-alanine (1.0 g, 4.2 mmol) was added followed by N-(3-dimethylaminopropyl)-N-ethylcarbodiimide hydrochloride (0.889 g, 4.6 mmol). Methylene chloride (10 mL) was added to dissolve the mixture. After 4 hours the reaction was extracted with methylene chloride (70 mL) and 1:4 saturated aqueous NaCl:saturated aqueous NaHCO$_3$ (20 mL). The organic layer was retained and dried over anhydrous Na$_2$SO$_4$. Solvent was removed by rotary evaporation under vacuum. The resulting thick oil was dissolved in acetonitrile (3 mL) and approximately ½ of the material was purified by HPLC on a waters symmetry shield C8 column (19×150 mm micron, 5 micron particle size). The column was eluted with deionized water containing 0.2% formic acid with an acetonitrile gradient (30%-60% acetonitrile over 18 min). The column was flushed with 95% acetonitrile for 5 min and then re-equilibrated with 30% acetonitrile for 6 min between runs. Injection volumes ranged between 100-800 uL. Unreacted maytansinol eluted at 8.5 min, an undesired isomer of Extra-NMA-DM1-SMe eluted at 13.8 min and the desired isomer of Extra-NMA-DM1-SMe eluted at 15.1 min. Fractions of desired product from several runs were combined and solvent was removed by rotary evaporation under vacuum. The residue was taken up in a minimum volume of ethyl acetate and a minor impurity was removed by HPLC on a Kromasil cyano column (250 mm×21 mm, 10 micron particle size). The column was run with an isocratic mobile phase of 67:9:24 hexanes:2-propanol:ethyl acetate at 21 mL/min. The desired product eluted at 22.6 min while the impurity eluted at 12.6 min. Product fractions from several runs were combined and solvent was removed by rotary evaporation under vacuum to provide 95 mg of product (10% yield). 1H NMR (400 MHz, CDCl$_3$-d) δ=7.26, 6.81 (d, J=1.6 Hz, 1H), 6.67 (d, J=11.1 Hz, 1H), 6.56 (d, J=1.6 Hz, 1H), 6.42 (dd, J=11.4, 15.2 Hz, 1H), 6.30 (s, 1H), 5.67 (dd, J=9.1, 15.2 Hz, 1H), 5.52-5.40 (m, 1H), 5.27 (d, J=7.1 Hz, 1H), 4.85-4.69 (m, 1H), 4.26 (t, J=10.9 Hz, 1H), 3.96 (s, 3H), 3.7 (bs, 1), 3.57 (d, J=12.6 Hz, 1H), 3.48 (d, J=8.8 Hz, 1H), 3.34 (s, 3H), 3.23 (s, 3H), 3.10 (d, J=12.6 Hz, 1H), 3.03-2.90 (m, 3H), 2.87 (s, 3H), 2.82-2.64 (m, 5H), 2.63-2.50 (m, 1H), 2.45-2.30 (m, 3H), 2.15 (d, J=14.1 Hz, 1H), 1.62 (s, 3H), 1.57 (d, J=13.6 Hz, 1H), 1.45 (d, J=6.3 Hz, 1H), 1.29 (d, J=7.1 Hz, 3H), 1.26 (d, J=6.3 Hz, 4H), 1.18 (d, J=6.3 Hz, 3H), 0.79 (s, 3H) 13C NMR (CDCl3, 100 MHz) δ 170.86, 170.50, 170.35, 168.69, 156.19, 152.35, 142.2, 140.90, 139.29, 133.27, 128.05, 125.1, 122.07, 119.15, 113.31, 88.72, 80.96, 78.51, 74.23, 66.19, 60.66, 60.13, 56.81, 56.71, 54.97, 47.90, 46.72, 38.99, 36.41, 35.68, 33.19, 32.54, 30.90, 30.02, 23.01, 15.62, 14.75, 14.59, 13.54, 12.35. HRMS calc. for C$_{40}$H$_{57}$ClN$_4$O$_{11}$S$_2$ (M+Na$^+$) m/z=891.3052; found 891.3049.

Example 10

Synthesis of Extra-NMA-DM1 (10)

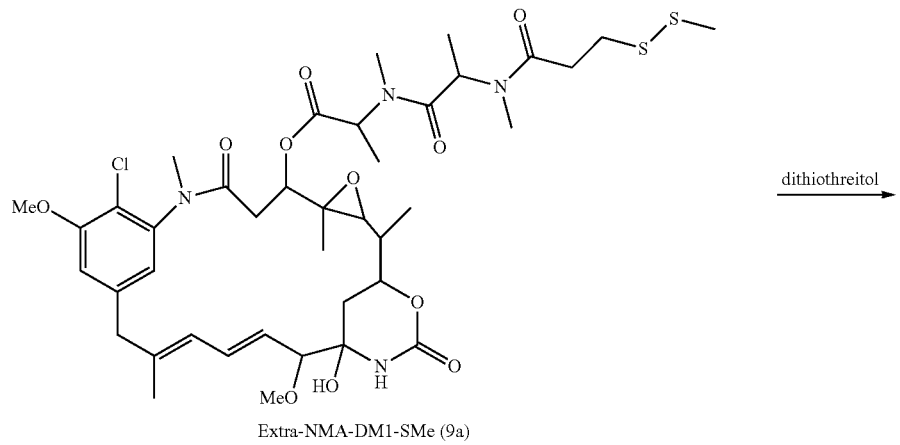

Extra-NMA-DM1-SMe (9a)

-continued
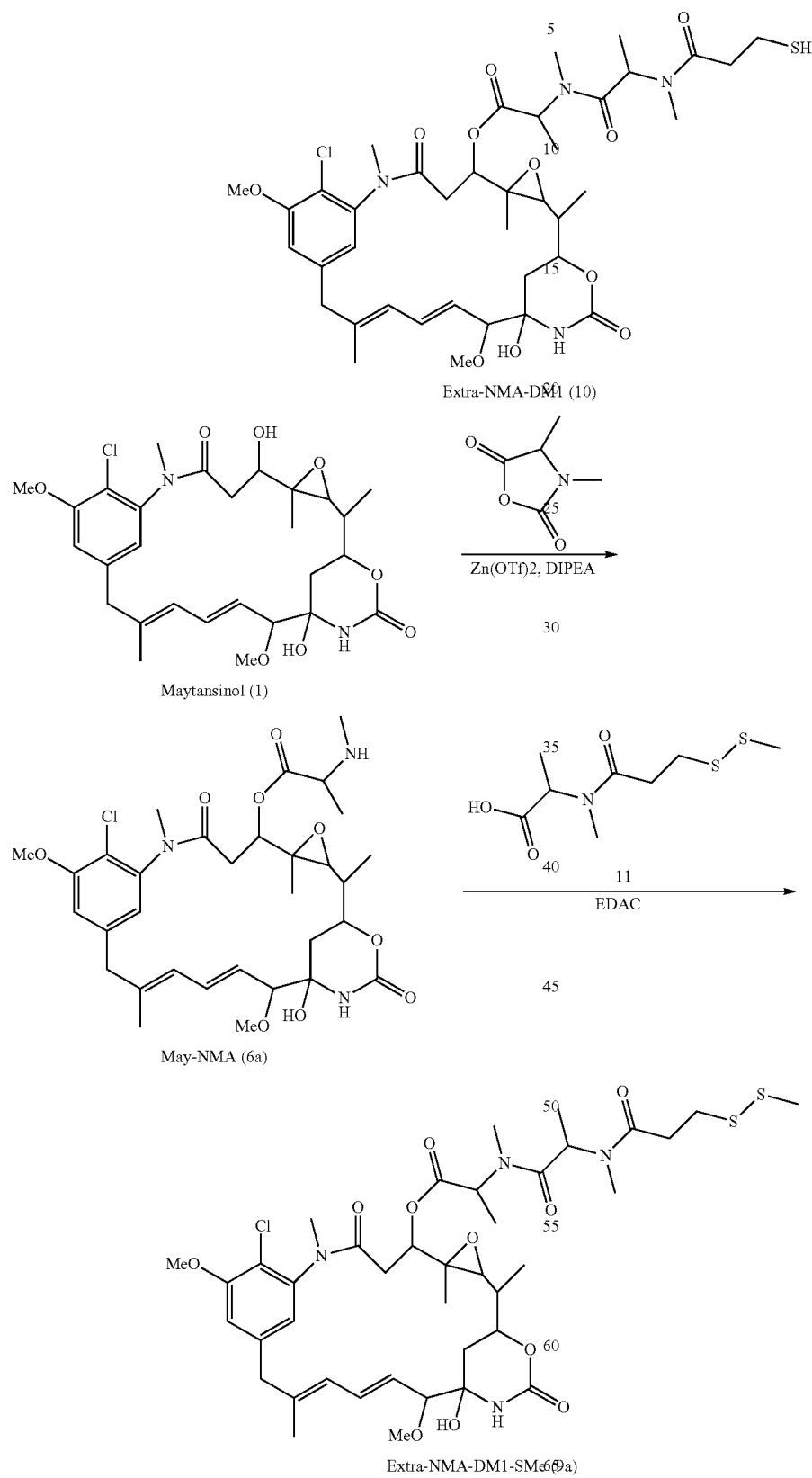

N2'-Deacetyl-N2'-(3-methyldithio-1-oxopropyl-N-methyl-L-alanyl)-maytansine (95 mg, 0.109 mmol) was dissolved in 2:1 dimethoxyethane:100 mM potassium phosphate buffer pH 7.5 to which dithiothreitol (110 mg, mmol) was added. After 2 hours the solution was extracted with a mixture ethyl acetate: methylene chloride=2: 1 (5 mL) and saturated aqueous NaCl (1 mL). The organic layer was retained and dried over anhydrous Na2SO4. The drying agent was removed by vacuum filtration and solvent was removed by rotary evaporation under vacuum. The residue was taken up in a minimum volume of 1:1 ethyl acetate:methylene chloride and purified by HPLC on a Kromasil cyano column (250 mm×21 mm, 10 micron particle size). The column was run with an isocratic mobile phase of 64:19:17 hexanes:2-propanol:ethyl acetate at 21 mL/min. Desired product eluted at 16 min. Fractions of product from several runs were combined end solvent was removed by rotary evaporation to provide 62 mg of product (69% yield). $^1$H NMR (400 MHz, CDCl$_3$) δ 6.81 (d, J=1.6 Hz, 1H), 6.67 (d, J=11.1 Hz, 1H), 6.58 (d, J=1.6 Hz, 1H), 6.43 (dd, J=15.3 Hz, 11.1 Hz, 1H), 6.26 (s, 1H), 5.67 (dd, J=15.3 Hz, 9.0 Hz, 1H), 5.47 (q, J=6.6 Hz, 1H), 5.28-5.22 (m, J=6.7 Hz, 1H), 4.81 (dd, J=12.0 Hz, 2.9 Hz, 1H), 4.26 (t, J=10.5 Hz, 1H), 3.96 (s, 3H), 3.59 (d, J=12.7 Hz, 1H), 3.49 (d, J=9.0 Hz, 1H), 3.41 (bs, 1H), 3.36 (s, 3H), 3.24 (s, 3H), 3.11 (d, J=12.7 Hz, 1H), 2.98 (d, J=9.6 Hz, 1H), 2.85 (s, 3H), 2.84-2.80 (m, 1H), 2.79 (s, 3H), 2.76 (s, 1H), 2.68-2.61 (m, 2H), 2.58 (d, J=12.1 Hz, 1H), 2.17 (dd, J=14.3 Hz, J=2.8 Hz, 1H), 1.71 (t, J=8.4 Hz, 1H), 1.64 (s, 3H), 1.62-1.59 (m, 1H), 1.49-1.40 (m, 1.31 (d, J=6.9 Hz, 3H), 1.29 (d, J=6.4 Hz, 3H), 1.27-1.23 (m, 1H), 1.20 (d, J=6.7 Hz, 3H), 0.81 (s, 3H). 13C NMR (CDCl3, 100 MHz) δ 170.37, 170.30, 170.25, 168.53, 156.07, 152.16, 142.31, 140.74, 139.16, 133.12, 127.09, 125.32, 121.92, 119.92, 113.15, 88.57, 80.83, 78.37, 74.08, 67.01, 59.97, 58.66, 56.56, 53.54, 49.17, 46.58, 38.86, 37.33, 36.25, 35.53, 32.39, 30.81, 29.80, 21.02, 19.87, 15.47, 14.80, 13.4, 12.22. HRMS calc. for C$_{39}$H$_{55}$ClN$_4$O$_{11}$S (M+Na$^+$) m/z=845.3174. found 845.3166.

What is claimed is:

1. A method of preparing a compound represented by the following formula:

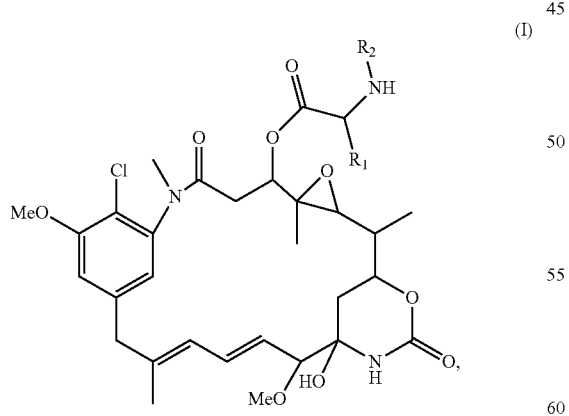

(I)

wherein R$_1$ is hydrogen, an optionally substituted C1-C10 alkyl group or an amino acid side chain, provided that, if the amino acid side chain has a reactive functional group, the reactive functional group is optionally protected; and R$_2$ is hydrogen or an optionally substituted C1-C10 alkyl group, the method comprising:

reacting maytansinol with an N-carboxyanhydride in a reaction mixture additionally comprising a base and a drying agent, wherein the N-carboxyanhydride is represented by the following formula:

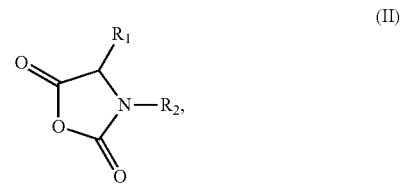

(II)

thereby forming the compound of Formula (I).

2. A method of preparing a compound represented by the following formula:

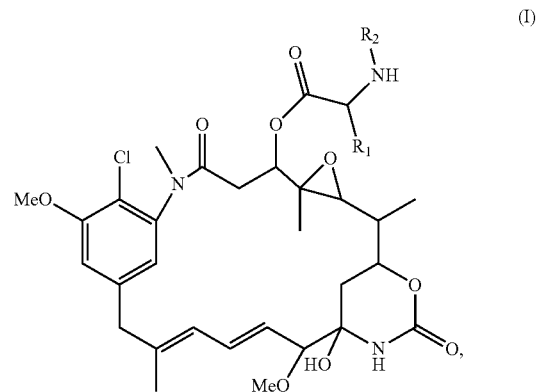

(I)

wherein R$_1$ is hydrogen, an optionally substituted C1-C10 alkyl group or an amino acid side chain, provided that, if the amino acid side chain has a reactive functional group, the reactive functional group is optionally protected; and R$_2$ is hydrogen, or an optionally substituted C1-C10 alkyl group, the method comprising:

a) reacting maytansinol with an N-carboxyanhydride in a reaction mixture additionally comprising a base, wherein the N-carboxyanhydride is represented by the following formula:

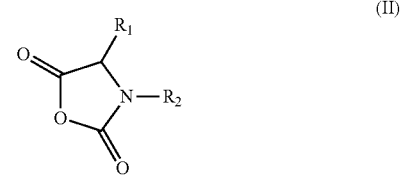

(II)

thereby forming the compound of Formula (I);

b) reacting unreacted N-carboxyanhydride from the reaction mixture in step a) with a nucleophilic reagent.

3. The method of claim 2, wherein the compound of Formula (I) is represented by the following formula:

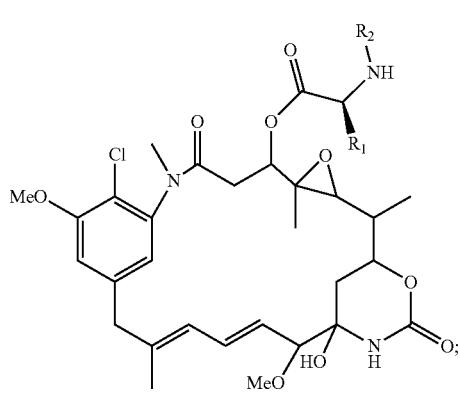

(Ia)

and the N-carboxyanhydride is represented by the following formula:

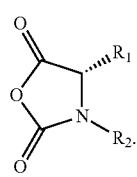

(IIa)

4. The method of claim 3, wherein the reaction mixture in step a) further comprises a Lewis acid.

5. The method of claim 4, wherein the Lewis acid is selected from the group consisting of zinc triflate, zinc chloride, magnesium bromide, magnesium triflate, copper triflate, copper (II) bromide copper (II) chloride, and magnesium chloride.

6. The method of claim 5, wherein the Lewis acid is zinc triflate.

7. The method of claim 5, wherein the reaction mixture in step a) further comprises a drying agent.

8. The method of claim 2, wherein the nucleophilic reagent is water or an alcohol.

9. The method of claim 8, wherein the alcohol is methanol, ethanol, n-propanol, isopropanol, or tert-butanol.

10. The method of claim 4, wherein the method further comprises contacting the reaction mixture after step b) with an aqueous solution containing bicarbonate or carbonate or contacting the reaction mixture with a metal scavenger.

11. The method of claim 2, further comprising the step of reacting the compound of formula (I) with a carboxylic acid having the formula $R_3COOH$ in the presence of a condensing agent or with an activated carboxylic acid having the formula $R_3COX$, to form a compound represented by the following formula:

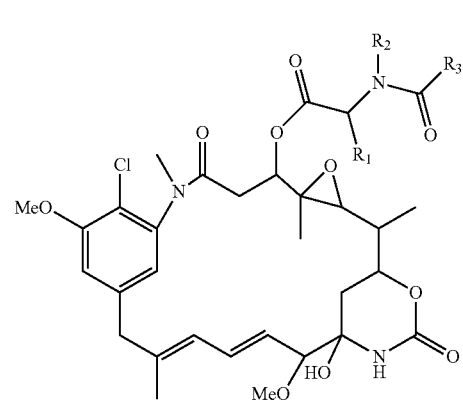

(III)

wherein $R_3$ is an alkyl group or a substituted alkyl group, and X is a leaving group.

12. The method of claim 11, wherein X is a halide, an alkoxy group, an aryloxy group, an imidazole, —S-phenyl optionally substituted with nitro or chloride, or —OCOR, in which R is a linear C1-C10 alkyl group, a branched C1-C10 alkyl group, a cyclic C3-C10 alkyl group, or a C1-C10 alkenyl group.

13. The method of claim 11, wherein —COX is a reactive ester.

14. The method of claim 11, wherein $R_3$ is —Y—S—$SR_4$, in which Y is C1-C10 alkylene and $R_4$ is C1-C10 alkyl, aryl, or heteroaryl.

15. The method of claim 14, wherein Y is —$CH_2CH_2$— or —$CH_2CH_2C(CH_3)_2$— and $R_4$ is —$CH_3$.

16. The method of claim 14, further comprising reacting the compound of formula (III) with a reducing agent to form a compound represented by the following formula:

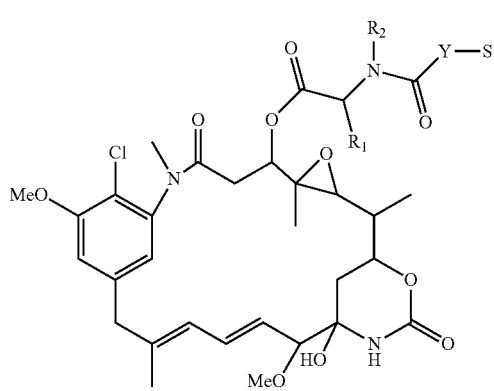

(IV)

17. The method of claim 11, wherein $R_3$ is -L-E; L is

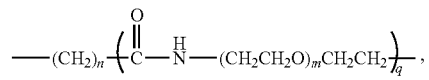

or —$(CH_2CH_2O)_mCH_2CH_2NHC(=O)CH_2CH_2$— or

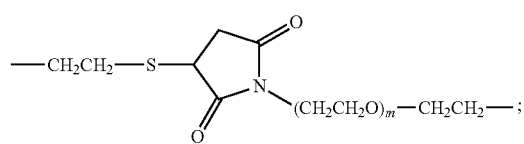
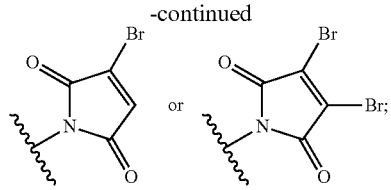
E is
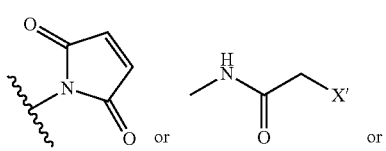
X' is a halide;
n is 2, 3, 4, 5 or 6;
m is 0 or an integer from 1 to 20; and
q is 0 or 1.
18. The method of claim 17, wherein L is —$(CH_2)_n$— or
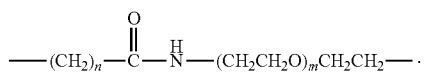
19. The method of claim 17, wherein $R_3$ is represented by one of the following:
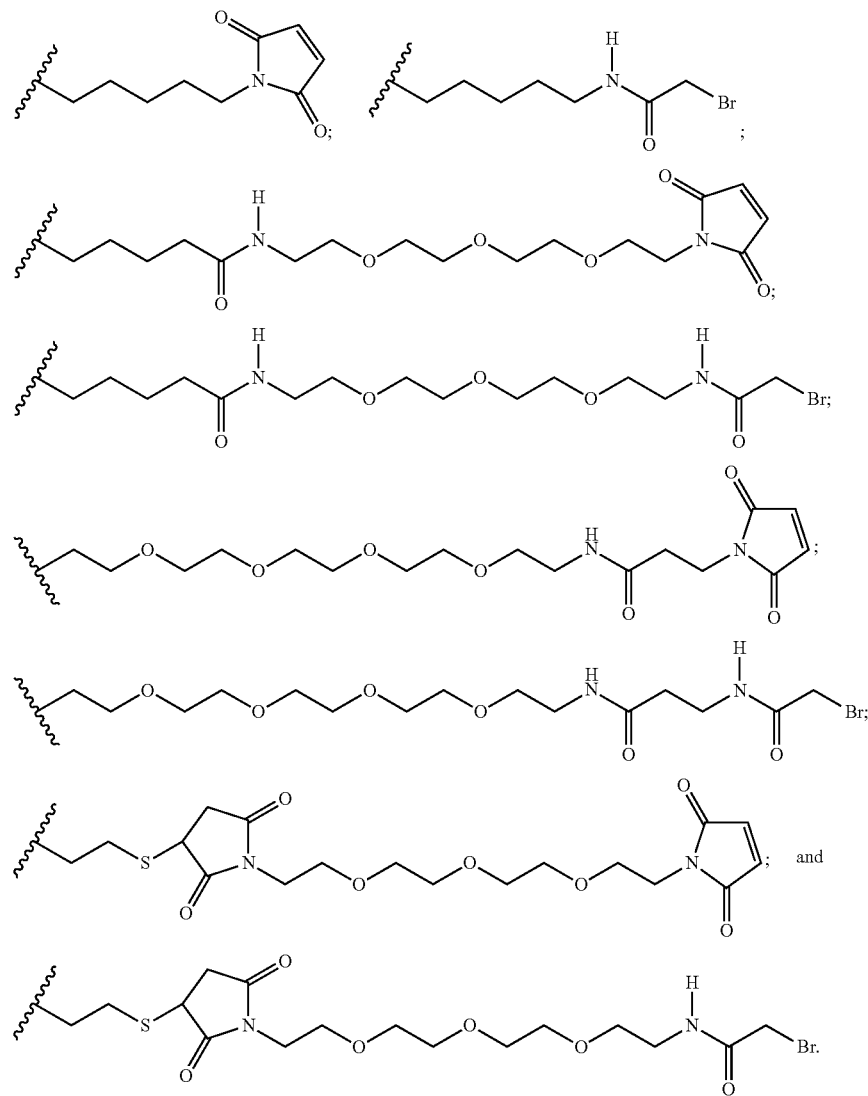

20. The method of claim 11, wherein the condensing agent is a carbodiimide, a uronium, an active ester, a phosphonium, 2-alkyl-1-alkylcarbonyl-1,2-dihydroquinoline, 2-alkoxy-1-alkoxycarbonyl-1,2-dihydroquinoline, or alkylchloroformate.

21. The method of claim 20, wherein the condensing agent is a carbodiimide.

22. The method of claim 21, wherein the condensing agent is N-(3-dimethylaminopropyl)-N'-ethylcarbodiimide hydrochloride.

23. The method of claim 2, wherein $R_1$ is methyl; and $R_2$ is methyl.

24. The method of claim 2, wherein the base is a trialkylamine, a metal alkoxide, an alkyl metal, an aryl metal, a metal hydride, a metal amide, or a silicon-based amide.

25. The method of claim 24, wherein the base is a trialkylamine.

26. The method of claim 25, wherein the trialkylamine is diisopropylethylamine.

27. The method of claim 7, wherein the drying agent is a molecular sieve, sodium sulfate, calcium sulfate, calcium chloride, or magnesium sulfate.

28. The method of claim 27, wherein the drying agent is a molecular sieve.

29. The method of claim 27, wherein the drying agent is in the form of granular beads or powders.

30. The method of claim 1, wherein the compound of Formula (I) is represented by the following formula:

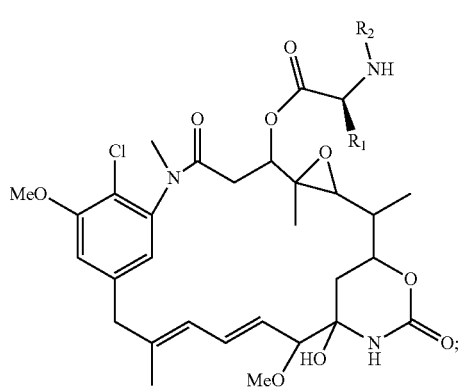

(Ia)

and the N-carboxyanhydride is represented by the following formula:

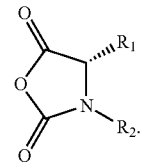

(IIa)

31. The method of claim 30, wherein the reaction mixture further comprises a Lewis acid.

32. The method of claim 31, wherein the Lewis acid is selected from the group consisting of zinc triflate, zinc chloride, magnesium bromide, magnesium triflate, copper triflate, copper (II) bromide, copper (II) chloride, and magnesium chloride.

33. The method of claim 31, wherein the Lewis acid is zinc triflate.

34. The method of claim 33, wherein further comprising contacting the reaction mixture after the reaction of maytansinol and the N-carboxyanhydride with an aqueous solution containing bicarbonate or carbonate or contacting the reaction mixture with a metal scavenger.

35. The method of claim 7, wherein the nucleophilic reagent is water or an alcohol.

36. The method of claim 1, wherein $R_1$ is methyl; and $R_2$ is methyl.

37. The method of claim 30, wherein $R_1$ is methyl; and $R_2$ is methyl.

38. The method of claim 3, wherein $R_1$ is methyl; and $R_2$ is methyl.

39. The method of claim 35, wherein $R_1$ is methyl; and $R_2$ is methyl.

* * * * *